(12) United States Patent
Stoellner et al.

(10) Patent No.: US 7,691,641 B2
(45) Date of Patent: Apr. 6, 2010

(54) POLYSACCHARIDE-PEPTIDE CONJUGATES FOR USE AS THROMBIN SUBSTRATES

(75) Inventors: Daniela Stoellner, Muttenz (CH); Thilo Henckel, Wetter (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 39 days.

(21) Appl. No.: 11/882,035

(22) Filed: Jul. 30, 2007

(65) Prior Publication Data

US 2008/0076183 A1     Mar. 27, 2008

(30) Foreign Application Priority Data

Jul. 31, 2006    (DE) ........................ 10 2006 035 899

(51) Int. Cl.
    *G01N 33/00*      (2006.01)
    *C07K 14/00*      (2006.01)
(52) U.S. Cl. ..................... 436/86; 530/330; 514/38; 514/39; 536/1.11; 536/127; 436/87
(58) Field of Classification Search .................. 436/86
See application file for complete search history.

(56) References Cited

U.S. PATENT DOCUMENTS 6,011,008 A     1/2000   Domb et al.

6,949,524 B2     9/2005   Singh et al.
7,390,525 B2 *   6/2008   Epstein et al. ............. 427/2.24
2007/0185040 A1 *   8/2007   Tor et al. ...................... 514/35

FOREIGN PATENT DOCUMENTS

| EP | 0 420 332 B1 | 4/1995 |
| EP | 1 247 870 A2 | 10/2002 |
| EP | 1 159 448 B1 | 4/2004 |
| EP | 1 669 761 A2 | 6/2006 |
| EP | 1 684 071 A2 | 7/2006 |
| WO | WO 00/52199 A3 | 9/2000 |
| WO | WO 01/70272 A1 | 9/2001 |
| WO | WO 02/10439 A2 | 2/2002 |
| WO | WO 2004/016807 A1 | 2/2004 |
| WO | WO 2006/125134 A1 | 11/2006 |

OTHER PUBLICATIONS

Hortin, G.L. et al., "Macromolecular Chromogenic Substrates for Measuring Proteinase Activity," *Clin. Chem.* 47(2):215-22 (2001).
Prasa, D. et al., "The Ability of Thrombin Inhibitors to Reduce the Thrombin Activity Generated in Plasma on Extrinsic and Intrinsic Activation," *Thromb. Haemost.* 77(3):498-503 (1997).

(Continued)

*Primary Examiner*—Krishnan S Menon
*Assistant Examiner*—Rebecca Fritchman
(74) *Attorney, Agent, or Firm*—Finnegan, Henderson, Farabow, Garrett & Dunner, L.L.P.

(57) ABSTRACT

The present invention relates to macromolecular polysaccharide-peptide conjugates which contain a peptide portion which C-terminally contains the amino acid sequence Ala-Gly-Arg, which is cleaved by thrombin.

17 Claims, 2 Drawing Sheets

OTHER PUBLICATIONS

Hemker et al., "A Computer Assisted Method to Obtain the Prothrombin Activation Velocity in Whole Plasma Independent of Thrombin Decay Processes," *Thrombosis and Haemostasis* 56:9-17 (1986).

Hemker et al., "Continuous Registration of Thrombin Generation in Plasma, Its Use for the Determination of the Thrombin Potential," *Thrombosis and Haemostasis* 70:617-24 (1993).

Hermanson et al., *Bioconjugate Techniques*, Academic Press, pp. 618-622 (1996).

* cited by examiner

POLYSACCHARIDE-PEPTIDE CONJUGATES FOR USE AS THROMBIN SUBSTRATES

This is application claims the benefit of German Application No. DE 10 2006 035899.6, filed Jul. 31, 2006, which is incorporated herein by reference.

BACKGROUND OF THE INVENTION

The regulation of blood clotting (hemostasis) is carried out by the interaction of various activators, inhibitors, and positive and negative feedback mechanisms. Defects in this system can lead to an imbalance in the hemostasis system and result in either a hemorrhage or thrombosis. Thrombin (factor IIa, F IIa) is a serine protease and the central enzyme of plasmatic blood clotting. The main function of thrombin consists in the induction of fibrin polymerization and is thus essential for clot formation. Thrombin is formed by activation of the enzymatically inactive precursor molecule prothrombin (factor II, F II). In order to restrict the clotting process to the site of injury, inhibitors of thrombin become activated as well. Via inhibition or by complexing the free thrombin, inhibitory factors such as, for example, antithrombin or $\alpha_2$-macroglobulin ($\alpha_2$-M) restrict and limit the coagulation process. An imbalance within the processes of thrombin formation and inhibition can lead to hypercoagulatory or hypocoagulatory states and thus to pathological clotting disorders. Thus, the measurement of thrombin formation and inhibition reveals important information about the particular clotting state of an individual patient.

Thrombin generation tests are global clotting tests, which determine the formation and inhibition of thrombin in plasma or blood. The inherent capacity, or in the case of plasma samples the plasma-intrinsic capacity, of a sample to form and inhibit enzymatically active, free thrombin is also known as the endogenous thrombin potential (ETP). Since all biological components that are contained in a test material and that influence the formation and the inhibition of thrombin affect the endogenous thrombin potential of a sample, the ETP determination is suitable both as a global test to detect a number of components of the hemostasis system and to monitor therapeutic measures. The ETP determination allows the diagnosis of hypocoagulatory and hypercoagulatory states. Further indications include hereditary and acquired coagulopathies (hemophilia, factor deficiency II, V, VII, VIII, IX, X, XI, disseminated intravascular coagulopathy) and thrombophilic risk factors (prothrombin mutation, factor V disease, protein S, protein C and antithrombin deficiency). Acquired and transient risk factors such as, for example, pregnancy, the use of oral contraceptives, and smoking are also reflected by increased ETP values. A further interesting aspect of ETP determination is the control of anticoagulation therapies. Since the capability of thrombin formation is determined directly, the clotting potential of the patient is detected independently of the anticoagulant(s) employed. Thus ETP measurement also offers a possibility of monitoring the transitional and stabilization phases of such therapies in order to avoid over-dosage and under-dosage.

Originally, for the determination of thrombin generation, a sample was treated with a prothrombin activator and aliquots were removed from the mixture at distinct time intervals. The thrombin concentration in the individual aliquots was determined by measuring the cleavage of a chromogenic thrombin substrate. Such a procedure, which is also known as the "subsampling method," is described, for example, in Hemker et al., "A computer assisted method to obtain the prothrombin activation velocity in whole plasma independent of thrombin decay process." *Thromb. Haemost.* 56 (1):9-17 (1986) on page 10 in the paragraph titled "Determination of the Time Course of Amidolytic Activity."

In EP 420 332 B1, an improved method for thrombin determination is described, which allows a continuous determination of the thrombin concentration in the reaction batch, such that the removal of a number of aliquots described above can be dispensed with. When continuously determining the thrombin concentration in a reaction batch, it is essential that the thrombin substrate used is not consumed before the thrombin inhibition is complete. The use of thrombin substrates, which have kinetic properties, such that they are reacted relatively slowly, but nevertheless proportionally to the amount of thrombin present, allows for continuous determination of the thrombin concentration in a single reaction batch. For determination of thrombin generation, the conversion kinetics of a thrombin substrate are measured in a sample of coagulable blood or plasma by means of the release of a detectable signal group. Since the thrombin substrate concentration is adjusted such that the substrate cannot be completely used up in the course of the reaction, the amount of released indicator ideally behaves proportionally to the enzymatic activity of the thrombin formed in the course of the clotting reaction (see also Hemker, H. C. et al., "Continuous registration of thrombin generation in plasma, its use for the determination of the thrombin potential." *Thromb. Haemost* 70(4)-617-24 (1993)).

In thrombin generation tests, small thrombin substrates of low molecular weight are customarily employed which comprise an oligopeptide to which is coupled a detectable signal group. By means of the enzymatic activity of thrombin, the bond between peptide and signal group is hydrolyzed, and the signal group is released. By means of the measurement of the signal strength, the thrombin activity can be quantified. Examples of oligopeptide substrates which, as is known, are cleaved by thrombin, are, for example, para-nitroanilide (pNA)-coupled peptides of the sequence Ala-Gly-Arg-pNA, Ala-Arg-pNA, Gly-Arg-pNA or Pro-Arg-pNA.

It is known, however, that with thrombin substrates which have a molecular size of less than 8 kD, the physiologically relevant activity of the free thrombin is measured in addition to the physiologically irrelevant activity of the $\alpha_2$-macroglobulin-thrombin complex ($\alpha_2$MT). From the measurement of the amount of released signal group over time, reaction kinetics result which, in spite of the progressive and finally complete inhibition of the free thrombin, reach no plateau phase. Instead, the reaction kinetics continue to increase. The small peptide substrates of low molecular weight are able to penetrate to the active center of the thrombin molecule through the $\alpha_2$-macroglobulin-thrombin complex ($\alpha_2$MT) and are therefore also cleaved by complexed thrombin. The amount of cleaved substrate is therefore not strictly proportional to the amount of free thrombin, but is the result of the activity of free and $\alpha_2$-macroglobulin-bound thrombin. Although various techniques for the calculation of the amount of free thrombin are known (e.g. EP 1 669 761 A2, WO 2004/016807 A1), these are relatively complicated in some cases. Alternative solutions that allow a direct determination of free thrombin on the basis of the experimental data are therefore desirable.

In EP 1 159 448 B1, the use of macromolecular ovalbumin-coupled thrombin substrates in a thrombin generation assay is described. Since ovalbumin-coupled thrombin substrates have a molecular size of more than 10 kDa, they are not cleaved by $\alpha_2$-macroglobulin-bonded thrombin, but only by free thrombin. The use of ovalbumin-coupled thrombin substrates, however, has disadvantages because technical problems occur when peptide substrates are coupled to ovalbumin when preparing the macromolecular substrate. Occasionally, the reaction solution is highly viscous, possibly on account of ovalbumin crosslinking reactions. The use of ovalbumin-coupled thrombin substrates is thus regarded as unsatisfactory because of problems in the preparation of these substrates and thus the restricted availability of the substrates. A further disadvantage in the use of protein-coupled macrosubstrates is that they cannot be added in higher concentrations, since precipitation reactions and thus turbidity can occur in the reaction batch. This is disadvantageous, in particular for test processes which are evaluated with the aid of optical methods.

SUMMARY OF THE INVENTION

The invention is in the field of diagnostics, in particular of coagulation diagnostics, and relates to the preparation and use of polysaccharide-peptide conjugates which contain a peptide portion which contains an amino acid sequence which is cleaved by thrombin.

The present invention was based on the object of providing further macromolecular thrombin substrates which are suitable for use in a thrombin generation test. Preferentially, the macromolecular substrates should not be cleaved by $\alpha_2$-macroglobulin-bonded thrombin. Also preferably, the macromolecular thrombin substrates should have kinetic properties, such that the thrombin substrate is not consumed before the thrombin inhibition is complete in a continuous thrombin generation test.

The present invention relates to a polysaccharide-peptide conjugate which is composed of a polysaccharide portion and a peptide portion and which has a molecular weight of more than 10 kDa. The peptide portion comprises a peptide of at least 3 amino acids whose C-terminus contains the sequence Ala-Gly-Arg-R, where R is a releasable signal group.

DESCRIPTION OF THE EMBODIMENTS

Figure 1:
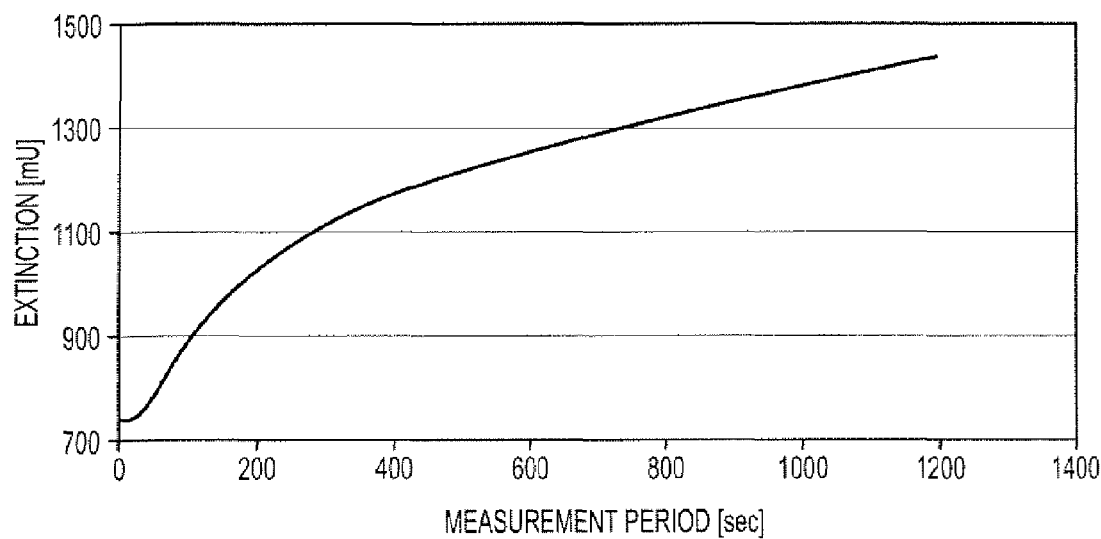
FIG. 1 shows a substrate conversion curve of the uncoupled, small molecular weight thrombin substrate β-Ala-Gly-Arg-pNA. After termination of thrombin formation and inhibition in the plasma sample, the reaction curve changes to a uniform, steady and linear increase, instead of reaching a plateau phase. This increase is based on the cleavage of the small molecular weight peptide substrate by $\alpha_2$-macroglobulin-bound thrombin.

The present invention was based on the object of providing further macromolecular thrombin substrates which are suitable for use in a thrombin generation test. Preferentially, the macromolecular substrates should not be cleaved by $\alpha_2$-macroglobulin-bonded thrombin. Also preferably, the macromolecular thrombin substrates should have kinetic properties, such that the thrombin substrate is not consumed before the thrombin inhibition is complete in a continuous thrombin generation test.

The present invention relates to a polysaccharide-peptide conjugate which is composed of a polysaccharide portion and a peptide portion and which has a molecular weight of more than 10 kDa. The peptide portion comprises a peptide of at least 3 amino acids whose C-terminus contains the sequence Ala-Gly-Arg-R, where R is a releasable signal group.

It has surprisingly been found that a polysaccharide-peptide conjugate which has the sequence Ala-Gly-Arg-R at the C-terminus of the peptide portion is suitable on account of its kinetic properties for use as a thrombin substrate in a thrombin generation test, whereas other polysaccharide-peptide conjugates which have another thrombin-specific peptide portion are not suitable for use in a continuous thrombin generation test because of their kinetic properties. The substrate according to the invention is cleaved by free thrombin, but not by $\alpha_2$-macroglobulin-bound thrombin. It is furthermore advantageous that the preparation of a polysaccharide-peptide conjugate according to the invention is more efficient than the problem-afflicted preparation of the ovalbumin-coupled thrombin substrates known from the prior art.

Polysaccharides or the polysaccharide portion of a conjugate according to the invention comprise identical or different monosaccharide units (homo- or heteropolysaccharides), which are connected to one another by means of glycosidic bonds. The structure of the polysaccharide molecule can be linear or branched. For the preparation of a polysaccharide-peptide conjugate according to the invention, polysaccharides are preferentially used which are constructed from monosaccharide units which contain vicinal diols or hydroxyl/amino groups or hydroxyl/carbonyl groups or carbonyl/carbonyl groups. Particularly preferred polysaccharides are, for example, dextran, galactan, arabinogalactan and mannan.

Preferentially, the polysaccharide portion of a conjugate according to the invention has a molar mass of approximately 10,000 to approximately 40,000 g/mol, preferably approximately 12,000 to approximately 20,000 g/mol, particularly preferably approximately 15,000 g/mol.

The peptide portion of a polysaccharide-peptide conjugate according to the invention comprises a peptide at least 3 amino acids long, whose C-terminus has the sequence Ala-Gly-Arg-R, where Ala is alanine, Gly is glycine, Arg is arginine and R is a cleavable signal group. The peptide can contain a few further amino acid residues N-terminally. Preferentially, the peptide comprises altogether a sequence of 3 to 5 amino acid residues, advantageously the peptide comprises not more than altogether 8 amino acid residues. Particularly preferably, the peptide comprises the tripeptide Ala-Gly-Arg.

The C-terminal signal group R is a signal group which can be cleaved by thrombin, which after removal from the arginine residue produces a detectable signal. The signal group can be, for example, a chromogenic or fluorogenic group which can be detected with the aid of photometric methods. Preferred chromogenic signal groups are para-nitroaniline (pNA), whose yellow color is measurable at a wavelength of λ=405 nm. A preferred fluorogenic group is 7-amino-4-methoxycoumarin (AMC).

Table 1 shows the kinetic properties of a dextran-β-Ala-Gly-Arg-pNA conjugate according to the invention in comparison to the kinetic properties of the uncoupled peptide substrate H-β-Ala-Gly-Arg-pNA or the dextran-coupled conjugates dextran-D-CHG-Ala-Arg-pNA and dextran-D-CHG-Gly-Arg-pNA.

TABLE 1

| | Km [mM] | Vmax [U] | Kcat [1/s] | Kcat/Km [L/mmol · s] |
|---|---|---|---|---|
| H-β-Ala-Gly-Arg-pNA 2AcOH | 2.2 | 16 | 17.4 | 7.9 |
| Dextran-β-Ala-Gly-Arg-pNA | 1.0-1.4 | 19.5 | 21 | 17.5 |
| Dextran-D-CHG-Ala-Arg-pNA * | 0.6 | 57 | 167 | 278 |
| Dextran-D-CHG-Gly-Arg-pNA * | 0.6 | 60 | 176 | 293 |

* D-CHG = D-2-cyclohexylglycine

In order to guarantee a continuous measurement of the thrombin generation, it is necessary that the substrate is reacted specifically, but as slowly as possible, by thrombin. The substrate concentration ($K_m$), also called the Michaelis constant, needed for the semisaturation of the enzyme is a measure of the substrate affinity to thrombin. In the case of high affinity, the substrate concentration $K_m$ is small, i.e. a small $K_m$ value is an expression of a high affinity for the respective substrate. The catalytic constant ($K_{cat}$), also called the turnover number, indicates the conversion rate of the enzyme or the number of substrate molecules, which are reacted by each active center in the enzyme molecule per unit time. The ratio $K_{cat}/K_m$ is designated the catalytic efficiency. This value is regarded as a measure of the substrate specificity, high values characterizing high substrate specificity. The maximum reaction rate $V_{max}$ designates the maximum conversion rate as a function of reaction conditions (e.g. pH, temperature) which also cannot be increased by a further increase in the substrate concentration (saturation of the reaction).

The uncoupled peptide substrate H-β-Ala-Gly-Arg-pNA and the dextran-coupled substrate dextran-β-Ala-Gly-Arg-pNA fulfill the requirements for a high $K_m$ value (low affinity to thrombin) and a low turnover number $K_{cat}$. In contrast to this, the dextran-peptide conjugates dextran-D-CHG-Ala-Arg-pNA and dextran-D-CHG-Gly-Arg-pNA exhibit clearly lower $K_m$ values (high affinity to thrombin) and a high turnover number $K_{cat}$. When using these two rapid substrates in a thrombin generation test, the reaction kinetics are steeper than when using the uncoupled peptide substrate H-β-Ala-Gly-Arg-pNA or the substrate according to the invention dextran-β-Ala-Gly-Arg-pNA, and substrate consumption rapidly occurs, whereby the proportionality of substrate conversion and thrombin concentration is no longer guaranteed.

The preparation of the polysaccharide-peptide conjugate according to the invention can be carried out by any desired process known to the person skilled in the art which allows a binding of a peptide containing the sequence Ala-Gly-Arg-R on its C-terminus, where R is a signal group cleavable by thrombin, to the polysaccharide. Processes for the preparation of polysaccharide-peptide conjugates are described, for example, in the patents U.S. Pat. No. 6,011,008, WO 01/70272 A1 and U.S. Pat. No. 6,949,524 B2. Preferred processes use an activated polysaccharide which has amine-reactive groups. Advantageous processes use a polyaldehyde-polysaccharide and a peptide portion that is coupled to the activated polysaccharide via formation of a Schiff's base. Typically, activation of the polysaccharide is necessary first in order to generate amine-reactive groups, such as, for example, aldehyde groups, in the polysaccharide molecule.

Processes are particularly preferred in which an activated polysaccharide is used which has 40 to 60, preferentially 45 to 55, aldehyde groups per polysaccharide molecule. The generation of the aldehyde groups can be carried out, for example, by oxidation with suitable oxidants, such as periodic acid or its salts such as, for example, sodium periodate ($NaIO_4$) (see, for example, Hermanson, G. T., Bioconjugate Techniques, Academic Press 1996, pages 618-622) or by use of alkylating substances, such as, for example, glycidyl ethers (see U.S. Pat. No. 6,949,524 B2).

In a preferred embodiment of a process for the preparation of a polysaccharide-peptide conjugate according to the invention, an activated dextran of a molar mass of approximately 15,000 to approximately 20,000 g/mol previously incubated in a 10% strength sodium metaperiodate solution for the generation of the aldehyde groups is used. A dextran activated in this way contains approximately 40 to 55 aldehyde groups. The degree of activation can be determined photometrically with the aid of the Purpald® method (Dickinson, R. G. and Jacobsen, N. W. "A new sensitive and specific test for the detection of aldehydes: formation of 6-mercapto-3-substituted-s-triazolo[4,3-b]-s-tetrazines." J. Chem. Soc. D. 1719-1720 (1970)). After a column chromatographic purification step in which, inter alia, excess sodium metaperiodate is removed, and rebuffering in carbonate buffer (pH 8.5), a 7.5- to 20-fold, particularly preferably a 10-fold, molar excess of peptide is added to the activated dextran. By adding a reducing substance to the reaction batch, such as, for example, of sodium or potassium borohydride, the Schiff's bases can be converted into more stable, secondary amine bonds. After a size-exclusion chromatographic purification step in which, inter alia, unbound peptide is removed, the conjugate, for example, can be lyophilized. In the case of conjugates prepared in this way, approximately 7 to 10 peptide molecules are bonded to one dextran molecule. The coupling result can be checked by means of HPLC (high performance liquid chromatography) analysis.

Polysaccharide-peptide conjugates are preferred in which at least 5, preferably at least 10, peptide molecules are bonded per polysaccharide molecule.

Polysaccharide-peptide conjugates are furthermore preferred in which the peptide portion is bonded to the polysaccharide via a secondary amine bond.

A further aspect of the present invention relates to the use of a polysaccharide-peptide conjugate according to the invention as a thrombin substrate in a process for the determination of thrombin generation. On account of their molecular size of at least 10 kDa, the use of the conjugates according to the invention is particularly advantageous if thrombin inhibitors such as $\alpha_2$-macroglobulin are present in the reaction batch. This is customarily the case if the thrombin generation is determined in blood or plasma samples. In a typical process for the determination of the thrombin generation, a blood or plasma sample of a patient is mixed with the thrombin substrate and clotting is induced by addition of a suitable activator. From the measurement of the amount of signal group released over time, reaction kinetics are plotted which in healthy people, after an initial lag phase, first change into an exponential phase of thrombin formation and finally reach a plateau phase with increasing inhibition of the thrombin. A particularly preferred use of a polysaccharide-peptide conjugate according to the invention is use as a thrombin substrate in a process for the determination of thrombin generation such as is described, for example, in EP 420 332 B1.

The following examples are provided for illustrative purposes only and are not intended to limit or restrict the scope of the invention.

EXAMPLES

Example 1

Preparation of the Dextran-Coupled Thrombin Substrate Dextran-β-Ala-Gly-Arg-pNA a) Oxidation of Dextran 1500 mg of dextran having a molecular weight of 15 to 20 kDa according to manufacturer's information (Fluka, Buchs, Switzerland) were dissolved in 30 ml of a 10% strength sodium metaperiodate solution and incubated for 24 hours at room temperature (19-26° C.) with protection from light. Excess sodium metaperiodate and by-products were separated off from the reaction batch by rebuffering in 0.1 M sodium hydrogencarbonate buffer (pH 8.5) on PD-10 ready-to-use columns (GE Healthcare, Uppsala, Sweden).

b) Coupling of β-Ala-Gly-Arg-pNA to Oxidized Dextran

A 10-fold molar excess of β-Ala-Gly-Arg-pNA peptide (Pefa 5134, Pentapharm, Basle, Switzerland) was added to the oxidized dextran (see Example 1a), and this solution was incubated for 24 hours at room temperature with protection from light. Fifteen minutes after the start of reaction, 0.2 ml of a 1 M sodium borohydride solution was added per milliliter of reaction solution. The reaction was stopped by addition of TRIS solution (pH 8.0) with a final concentration of 0.2 mol/l.

c) Purification of the Dextran-β-Ala-Gly-Arg-pNA Conjugate

In order to separate off non-coupled peptides or free pNA from the desired dextran-β-Ala-Gly-Arg-pNA conjugate, the conjugate was purified in 0.1% acetic acid by size-exclusion chromatography on a Sephacryl™ TMS-200 column (GE Healthcare, Uppsala, Sweden). After lyophilization, the yield of dextran-coupled substrate was 850 to 1400 mg. The dextran-β-Ala-Gly-Arg-pNA conjugate prepared in this way had a molecular weight of approximately 20 kDa.

The peptide substrates H-D-CHG-Ala-Arg-pNA (Pefa 5114, Pentapharm, Basle, Switzerland) and H-D-CHG-Gly-Arg-pNA (Pefa 081-04, Pentapharm, Basle, Switzerland) were coupled to dextran in the same manner and subsequently purified.

Example 2

Determination of the Degree of Activation of the Oxidized Dextran

For the determination of the degree of activation of the oxidized dextran, an aliquot was taken from the reaction solution which was obtained after oxidation of the dextran (see Example 1a) and this was diluted with 10 mM sodium phosphate/300 mM sodium chloride buffer. 100 µl of the diluted dextran solution were reacted for 45 minutes with 500 µl of a 1% strength Purpald® solution in 1 N sodium hydroxide solution. The reaction was subsequently stopped by addition of 400 µl of a 2 mg/ml sodium cyanoborohydride solution and the absorption at 540 nm was measured. The aldehyde concentration was determined by comparison of the absorption with a standard curve and the degree of activation was calculated from the aldehyde concentration/dextran concentration quotient.

According to the process described in Example 1a, oxidized dextran having a degree of activation of 40 to 55 aldehyde groups per dextran molecule was obtained.

Example 3

Determination of the Result of Coupling

For the determination of the result of coupling of the coupling described in Example 1b) of β-Ala-Gly-Arg-pNA to the oxidized dextran, non-bound peptide was quantified before and after coupling by means of HPLC analysis using a protein KW-803 column (Shodex, Japan) and by comparison with a peptide standard curve. From the quantitative difference in free peptide before and after coupling, the bound peptide fraction was calculated and this was related to the amount of dextran.

Per dextran molecule, 7 to 10 peptide molecules were bound.

Example 4

Figure 2:
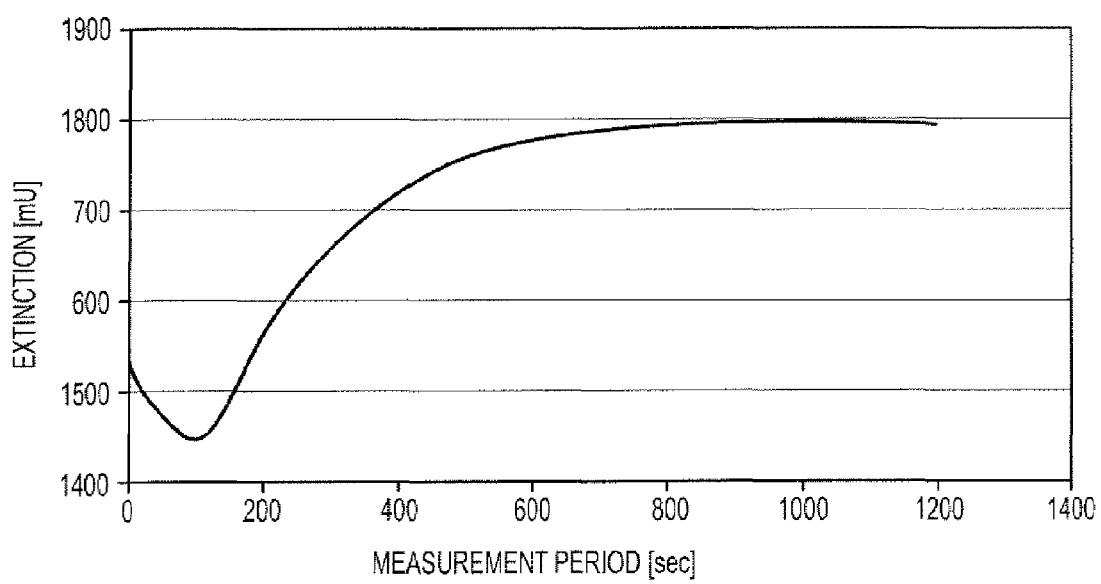
FIG. 2 shows a substrate curve of the macromolecular thrombin substrate dextran-β-Ala-Gly-Arg-pNA. After termination of thrombin formation and inhibition in the plasma sample, the reaction curve changes to an equilibrium state and reaches a plateau phase in which substrate conversion no longer takes place and the extinction remains constant. The substrate conversion in this case is directly proportional to the amount of free thrombin.
Figure 3:
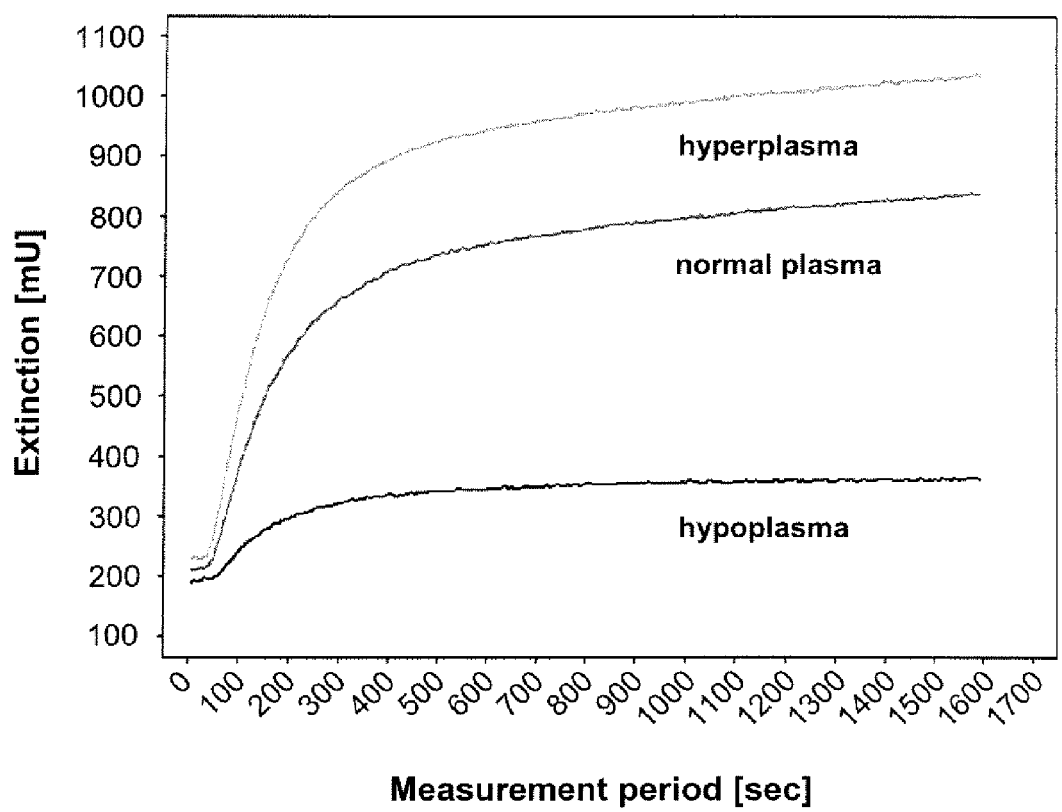
FIG. 3 shows the substrate curve of a normal plasma pool, of a plasma pool with decreased thrombin formation (hypopool) and of a plasma pool with increased thrombin formation (hyperpool). The reaction curve course and the endpoint of the change in extinction at the end of the reaction is dependent on the thrombin formation in the sample.

Use of the Dextran-β-Ala-Gly-Arg-pNA Conjugate According to the Invention as a Thrombin Substrate for the Determination of the Endogenous Thrombin Potential For the determination of the endogenous thrombin potential, the lyophilized thrombin substrate dextran-β-Ala-Gly-Arg-pNA (see Ex. 1) was dissolved in 1 ml of Tris HCl buffer [50 mM], pH 7.4 Subsequently, 135 µl of defibrinated platelet-poor plasma (PPP) were preincubated at 37° C. with 80 µl of this substrate solution. The thrombin generation was started by addition of 30 µl of Innovin® (reagent comprising recombinant human tissue factor and a mixture of synthetic phospholipids; Dade Behring Marburg GmbH, Germany) and 15 µl of $CaCl_2$ [250 mM]. Measurement was started simultaneously. The change in extinction was monitored for at least 20 minutes in a Behring coagulation system BCS® system (Dade Behring Marburg GmbH, Marburg, Germany) at a wavelength of $\lambda$=405 nm (see FIG. 2).

For comparison purposes, the determination of the endogenous thrombin potential was carried out in parallel using the uncoupled substrate H-β-Ala-Gly-Arg-pNA. The substrate solution used for this contained 1 mM H-β-Ala-Gly-Arg-pNA (see FIG. 1).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A polysaccharide-peptide conjugate having a molecular weight of more than 10 kDa, wherein the peptide portion comprises the sequence Ala-Gly-Arg-R on its C-terminus, wherein R is a signal group cleavable by thrombin, and wherein at least five peptide molecules are bonded per polysaccharide molecule.

2. The polysaccharide-peptide conjugate as claimed in claim 1, wherein the peptide portion comprises an amino acid sequence of three to five amino acid residues, wherein the peptide is not more than eight amino acid residues long.

3. The polysaccharide-peptide conjugate as claimed in claim 1, wherein the polysaccharide is constructed from monosaccharide units which contain vicinal diols or hydroxyl/amino groups or hydroxyl/carbonyl groups or carbonyl/carbonyl groups.

4. The polysaccharide-peptide conjugate as claimed in claim 1, wherein the polysaccharide portion comprises dextran.

5. The polysaccharide-peptide conjugate as claimed in claim 1, wherein the polysaccharide portion has a molar mass of approximately 10,000 g/mol to approximately 40,000 g/mol.

6. The polysaccharide-peptide conjugate as claimed in claim 1, wherein the cleavable signal group R is a chromogenic group.

7. The polysaccharide-peptide conjugate as claimed in claim 6, wherein the chromogenic group is para-nitroaniline (pNA).

8. The polysaccharide-peptide conjugate as claimed in claim 1, wherein the cleavable signal group R is a fluorogenic group.

9. The polysaccharide-peptide conjugate as claimed in claim 1, wherein the peptide portion is bonded to the polysaccharide via a secondary amine bond.

10. A method for the determination of thrombin generation in a sample, the method comprising
 (a) obtaining a blood or plasma sample of a patient,
 (b) mixing the sample with a polysaccharide-peptide conjugate and a suitable activator, and
 (c) measuring the amount of signal group released over time,
wherein the polysaccharide-peptide conjugate has a molecular weight of more than 10 kDa, wherein the peptide portion comprises the sequence Ala-Gly-Arg-R on its C-terminus, wherein R is a signal group cleavable by thrombin, and wherein at least five peptide molecules are bonded per polysaccharide molecule.

11. The polysaccharide-peptide conjugate as claimed in claim 5, wherein the polysaccharide portion has a molar mass of approximately 12,000 g/mol to approximately 20,000 g/mol.

12. The polysaccharide-peptide conjugate as claimed in claim 11, wherein the polysaccharide portion has a molar mass of approximately 15,000 g/mol.

13. The polysaccharide-peptide conjugate as claimed in claim 1, wherein at least ten peptide molecules are bonded per polysaccharide molecule.

14. The conjugate of claim 4, wherein the conjugate has a molecular weight of approximately 20 kDa.

15. The conjugate of claim 4, comprising seven to ten peptide molecules.

16. The conjugate of claim 8, wherein the fluorogenic group is 7-amino-4-methoxycoumarin (AMC).

17. The method of claim 10, wherein the activator is recombinant human tissue factor.

* * * * *